United States Patent [19]

Lee et al.

[11] 3,990,849
[45] Nov. 9, 1976

[54] SEPARATION OF CELLS FROM LIQUID COMPONENTS OF BLOOD

[75] Inventors: Martin J. Lee, Westwood, N.J.; Bruce J. Oberhardt, Bronx, N.Y.

[73] Assignee: Technicon Instruments Corporation, Tarrytown, N.Y.

[22] Filed: Feb. 7, 1975

[21] Appl. No.: 548,177

[52] U.S. Cl. .................. 23/230 B; 210/DIG. 23; 210/516; 356/36; 356/39
[51] Int. Cl.² ................ B01D 15/00; G01N 1/10; G01N 33/16
[58] Field of Search ............. 23/230 B, 283 R; 210/DIG. 23, 39, 40, 41, 516; 356/36, 39, 246; 195/103.5

[56] References Cited
UNITED STATES PATENTS

| 3,227,522 | 1/1966 | Salisbury, Jr. et al. | 23/253 R |
|---|---|---|---|
| 3,378,347 | 4/1968 | Saravis | 23/253 R |
| 3,401,087 | 9/1968 | Kuzel et al. | 23/230 B X |
| 3,674,438 | 7/1972 | Shen | 23/253 R |
| 3,692,486 | 9/1972 | Glenn | 23/230 B |
| 3,692,491 | 9/1972 | Trentelman | 23/253 R |
| 3,709,661 | 1/1973 | Hubscher | 23/253 R |
| 3,718,436 | 2/1973 | Ushakoff | 23/253 R |
| 3,762,877 | 10/1973 | Rains et al. | 23/230 B |

*Primary Examiner*—Robert M. Reese
*Attorney, Agent, or Firm*—S. P. Tedesco; Stephen E. Rockwell

[57] ABSTRACT

A method for separating a blood cell portion and a liquid portion of a whole blood sample comprising the steps of contacting over a period of time a substance in the form of a nonparticulate gel mass with the sample, so as to diffuse the liquid portion into the mass, the mass having an effective pore size to exclude the blood cells, and collecting the blood cells remaining after such contact of the sample with the mass. The method may include impregnating the substance of the mass with a selective reagent to react with the liquid portion diffused therein, and furthr include analyzing a reaction product produced within the mass.

13 Claims, 2 Drawing Figures

SEPARATION OF CELLS FROM LIQUID COMPONENTS OF BLOOD

BACKGROUND OF THE INVENTION

1. Field of the Invention

This invention relates to the separation of cells and the liquid components of blood utilizing a nonparticulate gel mass for the diffusion therein of the liquid components and for the exclusion of blood cells, so that the latter remain for collection.

2. Prior Art

It is known that substances may be separated from one another in time by an elution process utilizing a column packed with gel beads. In such a separation process all of the substances introduced into the column pass through the column. Such processes, referred to as gel filtration or gel permeation, require that the sample to be separated must not contain particulate matter comparable in size or larger than, the gel beads. Otherwise the column would become packed with the particulate matter to prevent the attempted separation. In this manner, blood platelets have been separated from the serum content of a specimen consisting of a mixture of platelets and serum. Platelets are considerably smaller than blood cells which, if introduced into such a column, would clog the column to such an extent as to render the elution process inoperative.

Other uses have been made of a nonparticulate gel mass supported as in a petri dish. One such use is in antibiotic susceptibility tests for example in which the gel is inoculated with microorganism, and a growth inhibitor in the form of a tablet is placed in the gel. Any area of nongrowth around the tablet is indicative of inhibition to growth due to the antibiotic. Another such use is one involving enzyme assays wherein a substrate is dispersed in the gel and reacts with a nonparticulate sample solution which diffuses into the gel for reaction therein. Still another use of such nonparticulate gel masses are antigen-antibody reactions in a typical one of which an antibody is located in the gel and the gel is exposed for diffusion thereinto of a nonparticulate solution of an antigen.

The present invention resides in a new use of such a nonparticulate gel mass, that is for the separation of a blood cell portion from a liquid portion of a whole blood sample. Such separation has heretofore been achieved by centrifugation of whole blood which has required the time consuming and burdensome steps of placing the whole blood sample in a suitable container in a centrifuge machine prior to analysis of the serum or plasma portion in an automated machine for example. Another procedure for such separation has been the settling of a whole blood sample in a well, perhaps, with the use of a settling agent, and then decanting the liquid portion for later use elsewhere in analysis of such liquid portion, as described in U.S. Pat. 3,146,163. However, even the last-mentioned procedure is burdensome to the user. Still another way of achieving such separation has been by utilizing an agglutinating agent in a whole blood sample for agglutination of the cells, which also requires decantation of the liquid portion.

The present invention overcomes these difficulties in the prior art.

SUMMARY OF THE INVENTION

One object of the invention is to provide an improved separation of a blood cell portion and a liquid portion of a whole blood sample. Another object is to provide such separation on-line in sample analysis.

More specifically, there is provided a method for separating a blood cell portion and a liquid portion of a whole blood sample comprising the steps of contacting over a period of time a substance in the form of a nonparticulate gel mass with the sample, so as to diffuse the liquid portion into the mass, the mass having an effective pore size to exclude the blood cells, and collecting the blood cells remaining after such contact of the sample with the mass. The method may include impregnating the substance of the mass with a selective reagent to react with the liquid portion diffused therein, and may further include analyzing a reaction product produced within the mass.

DETAILED DESCRIPTION OF THE PREFERRED EMBODIMENTS

Figure 1:
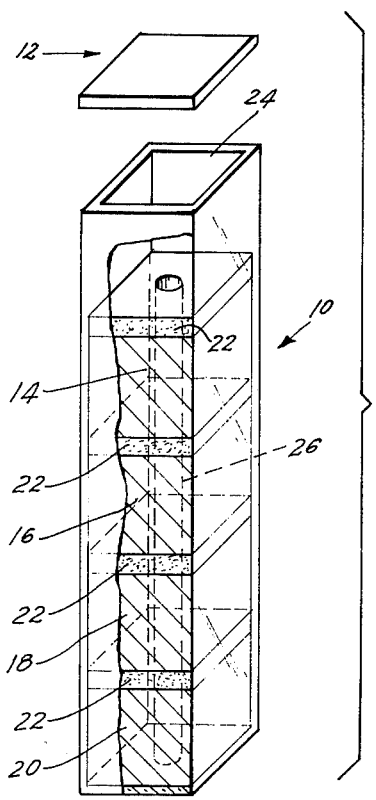
FIG. 1 is an isometric view, partially broken away, illustrating the novel article for carrying out the method of the invention.

In FIG. 1, there is shown an upstanding cuvette 10 having a cover 12. The cuvette is preferably of rectangular cross section for optical purposes and may be formed of inert clear glass or suitable inert, clear plastic material such as cellulose acetate butyrate, polyvinyl chloride or polyvinyl acetate, for example. The material of the cuvette and cover must be impervious to moisture and air. The cuvette has four walls and a bottom and is open at the top. The cover 12 has an air-tight seal with the cuvette when the cuvette is assembled and prior to use.

In the form chosen by way of example, the cuvette has within its plural stacked layers of nonparticulate gel masses 14, 16, 18, and 20 extending to all sides of the cuvette and separated one from another by a layer 22 of moisture-impervious material, such as wax for example, and the uppermost gel mass 14 has thereabove in overlying and abutting relation a layer 22 of such moisture-impervious material spaced below the top of the cuvette so as to provide a well 24 in the top of the cuvette 10. The well 24 has a reduced portion 26 extending centrally downwardly in all the above-described material within the cavity of the cuvette 10. The reduced portion 26 of the well may be circular in outline and have a diameter between 1–3 mm by way of example and not by way of limitation. In this example, the gel masses 14–20 may have a thickness between 10–40 mm, while the other dimensions of the gel masses may be approximately 10 × 10 mm. The moisture-impervious layers 22 may be approximately 1 mm thick.

The well portion 26 is provided to receive the whole blood sample to place the latter in contact with the gel masses 14–20, and the dimensions of the well portion 26 determine the volume of whole blood available for diffusion of the liquid portion thereof into the gel masses 14–20. The well portion 26 is filled when the cover 12 of the cuvette is removed. Any excess sample within the body is excluded from such contact with the gel masses by the uppermost layer 22 of barrier material so as to lie in the well enlargement 24 within the body above the last-mentioned layer. Each of the gel masses 14–20 has an effective pore size to exclude the blood cell portion of the sample of whole blood while allowing diffusion thereinto of a part of the liquid portion of the sample when such sample is in contact with the gel mass over a period of time, leaving the cell portion collected in the well portion 26. The gel, having such a pore size, is conventional in composition and may be that used and well known for precipitin reaction. In the illustrated form, the whole blood sample while in contact with the gel masses 14–20 is held in stagnant, captive condition within the well portion 26. Further, in this form, as the diffused liquid portion of the sample in each of the gel masses 14–20 is reacted therein with a different reagent in the gel mass to produce a different reaction product for optical analysis in the cuvette, quantitatively indicative of a different constituent of interest in the liquid portion of the sample, the substance of each gel mass must be selected so as to be clear and so as not to interfere with the particular sample-reagent reaction. Among other suitable gel materials for such selection are acrylamide, starch, agar, agarose, and gelatin, for example.

The above-described article may be assembled in the following manner. Starting with the lowermost substance, the selected gel-forming substance is liquified as by the application of heat and the selected reagent in the gel, is added to the liquid which is allowed to solidify as by cooling after being poured into the cuvette to form the gel mass 20. The moisture-impervious barrier material selected for the layer 22 directly above the gel mass 20, such as wax, is liquified as by the application of heat and poured on top of the gel mass 20 or it may be preformed and placed in the cuvette. It is allowed to solidify as by cooling. The process is repeated until all the gel masses, containing different reagents, and barrier layers 22 have been located in the cuvette. The well portion 26 may be formed by insertion of a rod-like die into the cuvette during the pouring and solidifying steps. However, it is presently considered preferable to form the well portion 26 after all pouring and solidifying steps by use of a suitable coring device. The cover 12 is then assembled with the cuvette 10 in air-tight relation for storage or handling of such cuvette prior to use.

By way of example, the reagent impregnated in the substance forming the gel mass 14 may be L-lactate and NAD for quantitation of lactic dehydrogenase in the sample liquid portion diffused into the gel mass 14 and reacted therein in the use of the article. Such diffusion and reaction may take approximately 5–10 minutes. The reagent in the gel mass 16 may be creatine phosphate, ADP, glucose, hexokinase, and NAD for quantitation of creatine phosphokinase. The reagents in the gel mass 18 may be alpha-ketoglutarate, aspartate, NADH, and malatedehydrogenase for quantitation of glutamate oxaloacetate transaminase. The reagent in gel mass 20 may be glucose oxidase, peroxidase, and o-dianisidine for quantitation of glucose.

Figure 2:
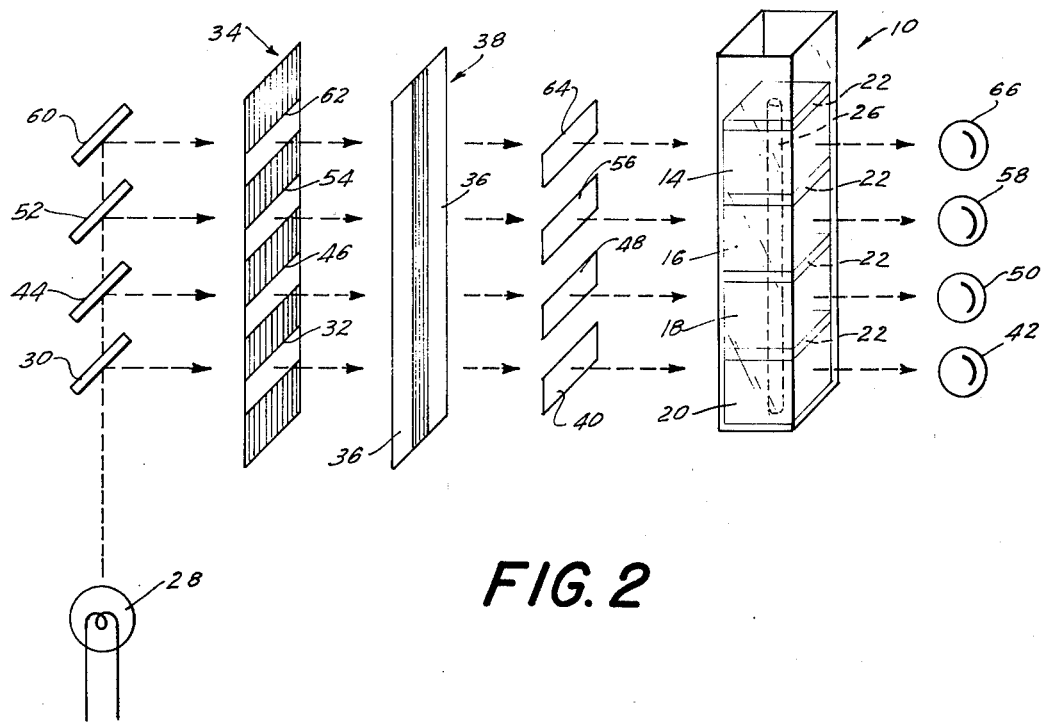
FIG. 2 is a view showing the article of FIG. 1 with the cover removed, associated diagramatically with apparatus for carrying out a novel method of analysis.

The whole blood sample is deposited in the cuvette 10 when the latter is in assembled condition with the analysis apparatus. As shown in FIG. 2, there is provided in such apparatus a light source 28 from which light is irradiated on a neutral beam splitter 30 which directs light to a 90° angle through a horizontal slit 32 in a mask 34, through a pair of laterally-spaced vertical slits 36 in a mask 38, through a filter 40 of appropriate wave length for the measurement, and through the diffused and reacted sample portion in the gel mass 20, to impinge on a photocell 42 which generates a signal according to the light transmitted or absorbed in the last-mentioned gel mass as a quantitative indication of the constituent of interest in the sample. The signal from the photocell 42 is processed and the result displayed in a conventional non-illustrated manner. The purpose of the mask 34 is to occlude the barrier layers 22 in the cuvette, and the purpose of the mask 38 is to occlude the well portion 26 in the cuvette. The beam splitter 30 passes light to impinge on a similar beam splitter 44 which directs light at a 90° angle through a horizontal slit 46 in the mask 34, through the horizontally-spaced vertical slits 36 in the mask 38, through a filter 48, and through the gel mass 18, to impinge on a photocell 50 similar to the photocell 42 and serving a similar function.

The beam splitter 44 passes light to impinge on a similar beam splitter 52 which directs light at a 90° angle through a horizontal slit 54 in the mask 34, through the pair of laterally-spaced vertical slits 36 in the mask 38, through a filter 56, and through the gel mass 16, to impinge on a photocell 58 similar to the photocell 42 and serving a similar function. The beam splitter 52 passes light to impinge on a mirror 60 which directs light at a 90° angle through a horizontal slit 62 in the mask 34, through the laterally-spaced vertical slits 36 of the mask 38, through a filter 64, and through the gel mass 14, to impinge on a photocell 66 similar to the photocell 42 and serving a similar function. In this manner, four parameters of the whole blood sample may be analyzed in the cuvette simultaneously, the four parameters in the illustrated form being lactic dehydrogenase, creatine phosphokinase, glutamate oxaloacetate transaminase and glucose. It is to be understood that while the illustrated cuvette contains four gel masses for these analyses, a similar cuvette may contain a greater number of such gel masses for an analysis of a larger number of parameters. However, on the other hand, it will be understood from the foregoing that the cuvette may contain a single reagent-impregnated, nonparticulate gel mass for analysis of a single parameter.

Another embodiment in which the invention may reside is that in which considerably thinner but similar nonparticulate gel mass approximately 1 mm thick, impregnated with a reagent is supported by a substrate which may be moisture-impervious, transparent tape. The last-mentioned gel mass has a sample-receiving well therein, and a number of such gel masses may be located at intervals along the length of the tape in such a form. The diffused, reacted sample portion in the gel mass is analyzed photometrically through the tape. The substance of each of the gel masses may have a different reagent therein for reaction with a portion of the same sample for a different analysis, or the reagent in each gel mass may be the same for reaction with different samples for the same analysis. Further, in such a configuration, it is desirable to place a moisture-impervious layer over such gel masses, which layer is transparent and through which the wells extend. Prior to such use of the tape, the wells may be covered by a moisture-proof material.

In the above described embodiments of the invention, it is important that the whole blood sample not clot. Such clotting would interfere with the aforementioned separation by diffusion of the sample in the gel mass. Hence, prior to the drawing of the blood from the donor in an evacuated container, the container is supplied with an anticoagulant selected so as not to interfere with the particular analysis or analyses to be conducted. It is believed that fresh blood, as from a finger prick, may be used in such a sample well for separation by diffusion prior to clotting. For such use of fresh blood, the gel-forming substance may be impregnated with an anticoagulant in the preparation of the gel. For these reasons, the portion of the sample which is diffused in the gel mass is neither described as serum nor plasma, but is described as the "liquid" portion of the whole blood sample. Such definition is generic to both plasma and serum.

While it has been stated with reference to the above-described forms that the reagent may be added in the preparation of the gel, it is to be understood that the reagent may be added in other ways which will be apparent to those versed in the art. For example, the reagent may be diffused in the gel. Further, the reagent may be one to stabilize or prepare the liquid sample portion for later use while not in the gel, but in a slurry in a continuous-flow analyzer such as that described in U.S. Pat. No. 3,241,432, for example.

In still another embodiment of the invention, a gel, for the diffusion thereinto of the liquid portion of whole blood sample but which diffused portion is not reacted for analysis, is located in a similar cuvette. The top of the gel mass is continuous, that is, it does not have a well formed therein, and the gel is located a distance below the top of the cuvette. The upper covering layer 22 of moisture-impervious material is omitted. In use, the whole blood sample provided with an anticoagulant as above, is poured into the top of the cuvette to form a layer over the gel mass. The liquid portion of the sample is diffused into the gel mass over a period of time, such as to allow the dissolved substances of the blood to enter the gel. The cell portion is then flushed out of the cuvette utilizing a saline solution. The flushed cells in saline are preferably layered on a fresh nonparticulate gel mass in another cuvette to remove remaining dissolved components. The cells are once again washed out with saline solution and recollected. The blood cells may then be appropriately handled in the conventional way for analysis of such cells.

While several of the preferred forms of the invention have been described above, it will be appparent, especially to those versed in the art, that the invention in separation of cells from the liquid components of blood may take other forms and is susceptible to various changes in details without departing from principles of the invention.

What is claimed is:

1. A method for separating a blood cell portion and a liquid portion of a whole blood sample, comprising the steps of: contacting over a period of time a substance in the form of a nonparticulate gel mass with said whole blood sample, so as to diffuse the liquid portion thereof into said gel mass, said gel mass having an effective pore size to exclude the blood cell portion, and collecting the blood cell portion remaining after contact of said sample with said gel mass.

2. A method as defined in claim 1, further including the step of holding said sample in a stagnant, captive condition while the latter is in contact with said gel mass.

3. A method as defined in claim 1, further including impregnating said substance with a selective reagent to react with said liquid sample portion when the latter is diffused in said gel mass.

4. A method as defined in claim 3, further including the step of analyzing the product produced within said gel mass on reaction of said reagent and said sample portion.

5. A method as defined in claim 1, further including forming a well in said gel mass, said collecting of the blood cell portion comprising collecting said cell portion in said well, and said contacting of said gel mass with said sample comprising introducing said sample into said well.

6. A method as defined, in claim 5, further including impregnating said substance with a selective reagent to react with said liquid sample portion when the latter is diffused in said gel mass and photometrically analyzing the reaction product produced within said gel mass by directing a beam of light through said gel mass.

7. A method as defined in claim 1, further including supporting plural ones of said gel masses in separated condition from one another, impregnating each substance forming one of said gel masses with a reagent, to react with a diffused part of said sample liquid portion said contacting step comprising contacting all said gel masses with said sample for diffusion into the respective gel masses of different parts of said sample liquid portion.

8. A method as defined in claim 7, wherein: said step of supporting said gel masses comprises stacking said gel masses with moisture-impervious barriers therebetween, said impregnating step comprises impregnating the substance of each gel mass with a different reagent to react with a part of the sample liquid portion when the latter is diffused thereinto, and analyzing the different reaction products in all said gel masses.

9. A method as defined in claim 9, wherein: said analyzing step includes concurrently analyzing all said reaction products.

10. An article, comprising: a substrate, means supported from said substrate for separating a whole blood sample into a cell portion and a liquid portion when contacted over a period of time with said sample, said means comprising a nonparticulate gel mass for diffusion thereinto of said liquid portion, said gel mass having an effective pore size to exclude said cell portion, and a selected reagent in said gel mass to react with said sample portion when the latter is diffused into said gel mass, said gel mass defining a sample-receiving well therein, said substrate comprising an upright cuvette within which said gel mass is vertically supported and further including a moisture-impervious barrier above said gel mass in abutment therewith and located a distance below the top of said cuvette, said barrier defining a vertical opening therethrough forming a part of said well, said cuvette and said barrier defining a well enlargement.

11. An article as defined in claim 10, wherein: said means comprises plural ones of said gel masses supported in separated condition from one another for contact with respective parts of said sample, and further including a different reagent in each gel mass for reaction with a different part of said sample liquid portion diffused in said mass.

12. An article as defined in claim 10, wherein: said means comprises plural ones of said gel masses supported in separated condition from one another for contact with respective parts of said sample, said gel masses being in vertically stacked relation with moisture-impervious barriers therebetween, said gel masses and said barriers defining a vertical common sample-receiving well.

13. An article as defined in claim 12, further including a moisture-impervious barrier directly above the uppermost one of said gel masses and located a distance below the top of said cuvette, the last-named barrier defining an opening forming a part of said common well, said cuvette and the last-named barrier defining a well enlargement.

* * * * *